(12) United States Patent
Vere Hodge et al.

(10) Patent No.: US 7,045,525 B1
(45) Date of Patent: May 16, 2006

(54) USE OF (R)-PENICICLOVIR TRIPHOSPHATE FOR THE MANUFACTURE OF A MEDICAMENT FOR THE TREATMENT OF VIRAL DISEASES

(75) Inventors: Richard Anthony Vere Hodge, Reigate (GB); Raymond F Schinazi, Decatur, GA (US)

(73) Assignee: Novartis AG, Basel (CH)

( * ) Notice: Subject to any disclaimer, the term of this patent is extended or adjusted under 35 U.S.C. 154(b) by 630 days.

(21) Appl. No.: 08/945,249

(22) PCT Filed: Apr. 23, 1996

(86) PCT No.: PCT/EP96/01706

§ 371 (c)(1),
(2), (4) Date: Feb. 2, 1998

(87) PCT Pub. No.: WO96/33720

PCT Pub. Date: Oct. 31, 1996

(30) Foreign Application Priority Data

Apr. 24, 1995 (GB) .................................... 9508237
Mar. 8, 1996 (GB) .................................... 9604909

(51) Int. Cl.
*A61K 31/522* (2006.01)
*A61K 31/675* (2006.01)

(52) U.S. Cl. ............................ 514/263.38; 514/263.37; 514/81

(58) Field of Classification Search ................ 514/262, 514/263.38, 263.37, 81
See application file for complete search history.

(56) References Cited

FOREIGN PATENT DOCUMENTS

| EP | 0 388 049 | 9/1990 |
| WO | WO 92/00742 | 1/1992 |

OTHER PUBLICATIONS

Mok et al., *Abstracts of the Interscience Conference on Antimicrobial Agents and Chemotherapy*, Abstracts No. H66, 35(0), p. 191 (1995).
Schinazi et al., *Abstracts of the Interscience Conference on Antimicrobial Agents and Chemotherapy*, Abstract No. H104, 35(0), p. 198 (1995).
Earnshaw et al., *Antimicrob. Agents Chemother.*, 36(12), pp. 2727-2757 (1992).
Vere Hodge et al., *Antiviral Chemistry & Chemotherapy*, 4(Supplement 1), pp. 13-24 (1993).
Abstacts of the 35th Interscience Conference on Antimicrobial Agents and Chemotherapy, Session 43, p. 182 and p. 191 (Sep. 17-20, 1995).
Program and Abstracts of the Eighth International Conference on Antiviral Research, Poster Session II, p. A304 (Apr. 23-28, 1995).

*Primary Examiner*—Shengjun Wang
(74) *Attorney, Agent, or Firm*—Regina Bautista

(57) ABSTRACT

A method of treatment of: i) HIV-1 infections in mammals, including humans; or ii) HBV infections in mammals, including humans; which method comprises the administration to the human in need of such treatment, an effective amount of the (R)-enantiomer of the triphosphate of a compound of formula (A) or a pharmaceutically acceptable salt thereof; and compounds for use in the method.

6 Claims, No Drawings

USE OF (R)-PENICICLOVIR TRIPHOSPHATE FOR THE MANUFACTURE OF A MEDICAMENT FOR THE TREATMENT OF VIRAL DISEASES

This application is a 371 of PCT/EP96/01706, filed Apr. 26, 1996, which claims foreign priority of UK 9508237.6 filed Apr. 24, 1995, and UK 9604909.3, filed Mar. 8, 1996.

This invention relates to treatment of human immunodeficiency virus (HIV) and hepatitis B virus (HBV) infection.

When used herein, 'treatment' includes prophylaxis as appropriate.

EP-A-141927 (Beecham Group p.l.c.) discloses penciclovir (PCV), the compound of formula (A):

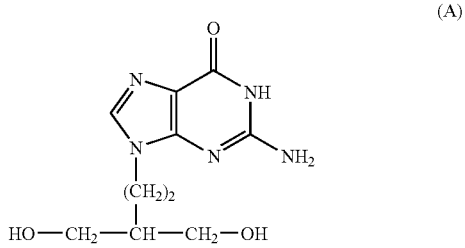

(A)

and salts, phosphate esters and acyl derivatives thereof, as antiviral agents. The sodium salt hydrate of penciclovir is disclosed in EP-A-216459 (Beecham Group p.l.c.). Penciclovir and its antiviral activity is also disclosed in Abstract P.V11–5 p. 193 of 'Abstracts of 14th Int. Congress of Microbiology', Manchester, England 7–13 Sep. 1986 (Boyd et. al.).

Orally active bioprecursors of the compound of formula (A) are of formula (B):

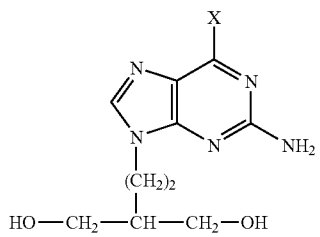

(B)

and salts and derivatives thereof as defined under formula (A); wherein X is $C_{1-6}$ alkoxy, $NH_2$ or hydrogen. The compounds of formula (B) wherein X is $C_{1-6}$ alkoxy or $NH_2$ are disclosed in EP-A-141927 and the compounds of formula (B) wherein X is hydrogen, disclosed in EP-A-182024 (Beecham Group p.l.c.) are preferred prodrugs. A particularly preferred example of a compound of formula (B) is that wherein X is hydrogen and wherein the two OH groups are both in the form of the acetyl derivative, described in Example 2 of EP-A-182024, hereinafter referred to as famciclovir.

EP-A-388049 (Beecham Group p.l.c.), discloses the use of penciclovir/famciclovir in the treatment of hepatitis B virus infection.

The antiviral activity against hepatitis B virus appears to be dependent on intracellular formation of penciclovir triphosphate (PCV-TP). The HBV polymerase has many enzymatic activities, including formation of a covalent bond between the polymerase and dGMP, addition of T-A-A, followed by RNA-directed DNA polymerase (reverse transcriptase) and DNA-directed DNA synthesis.

The triphosphate derivative of penciclovir inhibits the RNA-directed DNA polymerase (reverse transcriptase) activity of human immunodeficiency virus type 1 (HIV-1). The reverse transcriptase of HIV-1 is a virus-encoded enzyme essential for the conversion of genomic RNA into proviral ds-DNA.

It has now been shown that the (R)-enantiomer of PCV-TP is more active than the (S)-enantiomer in respect of inhibition of HBV DNA polymerases and in respect of inhibition of HIV-1 reverse transcriptase.

Accordingly, the present invention provides a method of treatment of:

i) HIV-1 infections in mammals, including humans; or
ii) HBV infections in mammals, including humans;

which method comprises the administration to the human in need of such treatment, an effective amount of the (R)-enantiomer of the triphosphate of a compound of formula (A):

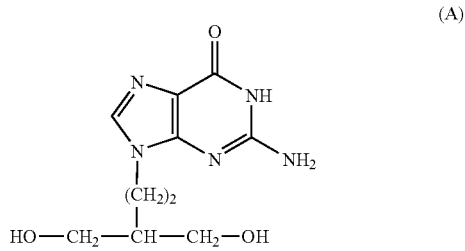

(A)

or a pharmaceutically acceptable salt thereof.

The (R)-PCV-TP is administered in the form of a compound which is a bioprecursor to allow absorption and penetration through the cell wall. Selectivity for the virus infected cell, especially HIV infected cells, can be achieved by selecting a bioprecursor which is activated preferentially by the virally encoded protease. The bioprecursor may be in the form of a derivative of (R)-PCV-MP which liberates intracellularly (R)-PCV-MP which is in turn converted to (R)-PCV-TP.

The compound may be administered by the oral route to humans and may be compounded in the form of syrup, tablets or capsule. When in the form of a tablet, any pharmaceutical carrier suitable for formulating such solid compositions may be used, for example magnesium stearate, starch, lactose, glucose, rice, flour and chalk. The compound may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. Sustained release formulations, for example tablets containing an enteric coating, are also envisaged.

For parenteral administration, fluid unit dose forms are prepared containing the compound and a sterile vehicle. The compound depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

A suitable dosage unit might contain from 50 mg to 1 g of active ingredient, for example 100 to 500 mg. Such doses may be administered 1 to 4 times a day or more usually 2 or 3 times a day. The effective dose of compound will, in general, be in the range of from 0.2 to 40 mg per kilogram of body weight per day or, more usually, 10 to 20 mg/kg per day.

The present invention also provides the use of the (R)-enantiomer of the triphosphate of a compound of formula (A) or a bioprecursor therefor, in the preparation of a medicament for use in the treatment of:
i) HIV-1 infections in mammals, including humans; or
ii) HBV infections in mammals, including humans.

Such treatment may be carried out in the manner as hereinbefore described.

The present invention further provides a pharmaceutical composition for use in the treatment of:
I) HIV-1 infections in mammals, including humans; or
ii) HBV infections in mammals, including humans;
which comprises an effective amount of the (R)-enantiomer of the triphosphate of a compound of formula (A), or a bioprecursor therefor, and a pharmaceutically acceptable carrier.

Such compositions may be prepared in the manner as hereinafter described.

The biological data describing the activity of (R)-PCV-TP is described by Shaw et al, Zoulim et al in 'Abstracts of the 35th Interscience Conference on Antimicrobial Agents and Chemotherapy' 17–20 Sep. 1995, H13, p182 and H36, p191 and Schinazi et al in 'Antiviral Research' 1995, Supplement 1, 146, A304, and also in the attached draft manuscript by Zoulim and the attached extract from the poster presented in support of the Schinazi reference, submitted with British Patent Application 9604909.3, from which the present application claims convention priority.

The following examples illustrate bioprecursors of the (R)-enantiomer of the triphosphate of a compound of formula (A). Examples 1, 2 and 5 are of potential interest in treatment of HBV and Examples 3 and 4 are of potential interest in treatment of HIV-1.

Example 1
PL-ASOR derivative

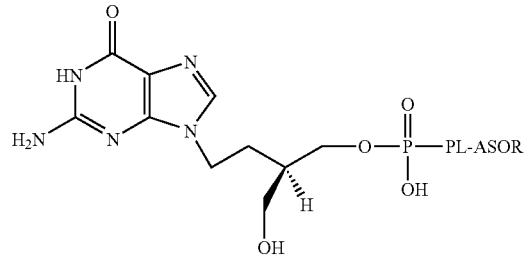

The (S) enantiomer of a PCV derivative with a protecting group on one hydroxyl group is phosphorylated and the the protecting group is then removed to afford (R)-PCV-MP. (R)-PCV-MP is activated and coupled to PL-ASOR by a procedure such as that described in Drug Delivery 2, 136, 1995. The resulting conjugate may have multiple (R)—PCV-MP moieties per protein molecule.

Example 2
Phospholipid derivative

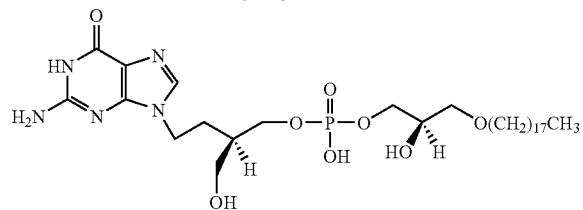

(R)-PCV-MP or a protected form thereof (prepared as in Example 1) is converted to this derivative by alkylation, or the phosphate group is activated and coupled to a protected form of the lipid, followed by deprotection.

Example 3
(R)-MP Bis(POM) derivative

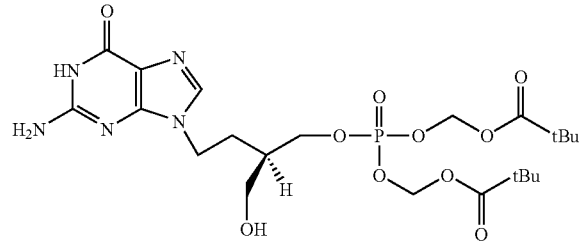

(R)-PCV-MP or a protected form thereof (prepared as in Example 1) is converted to the bis(POM) derivative by alkylation with pivalyloxymethyl chloride by the procedure of J. Pharmaceutical Sci. 72, 324–5, 1983 or of J. Med. Chem. 38, 1372–9, 1995 and the optionally present protecting group is removed.

Example 4
(R)-MP Diphenyl ester

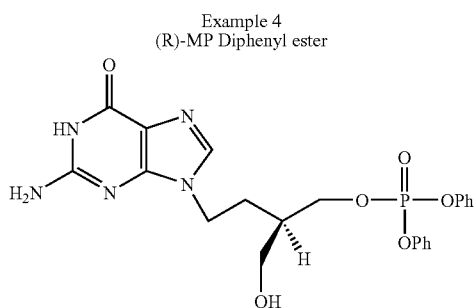

The (S) enantiomer of a PCV derivative with a protecting group on one hydroxyl group is treated with diphenyl phosphorochloridate and the protecting group is removed.

(R)-PCV-MP or a protected form thereof (prepared as in Example 1) is coupled with an activated form of sn-1,2-dimyristoylglycerol phosphate and the optionally present protecting group is removed.

DESCRIPTION 1—PREPARATION OF (R)—PCV PHOSPHATE

Retrosynthetic analysis of (R)-penciclovir triphosphate 1a yields the monoprotected synthon 2a, scheme 1. Further disconnection yields the chiral fragment 3a and 2-amino-6-chloropurine 4. The synthetic equivalent of the synthon 3a is the urethane 5a used by Kishi et al in the total synthesis of monensin[2]. By analogy for the synthesis of (S)-penciclovir triphosphate 1b requires the urethane 5b as starting material. The urethanes 5a and 5b have also been employed in the synthesis of (R)- and (S)-1-(3-hydroxymethylpyrrolidin-1-yl)cytosine[3].

Exmple 5
Dimyristoylglycerol diphosphate derivative

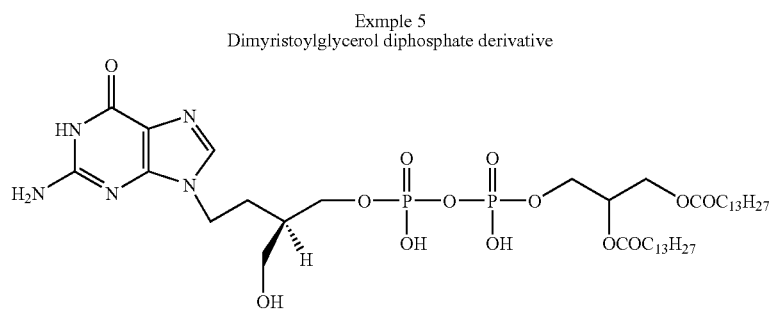

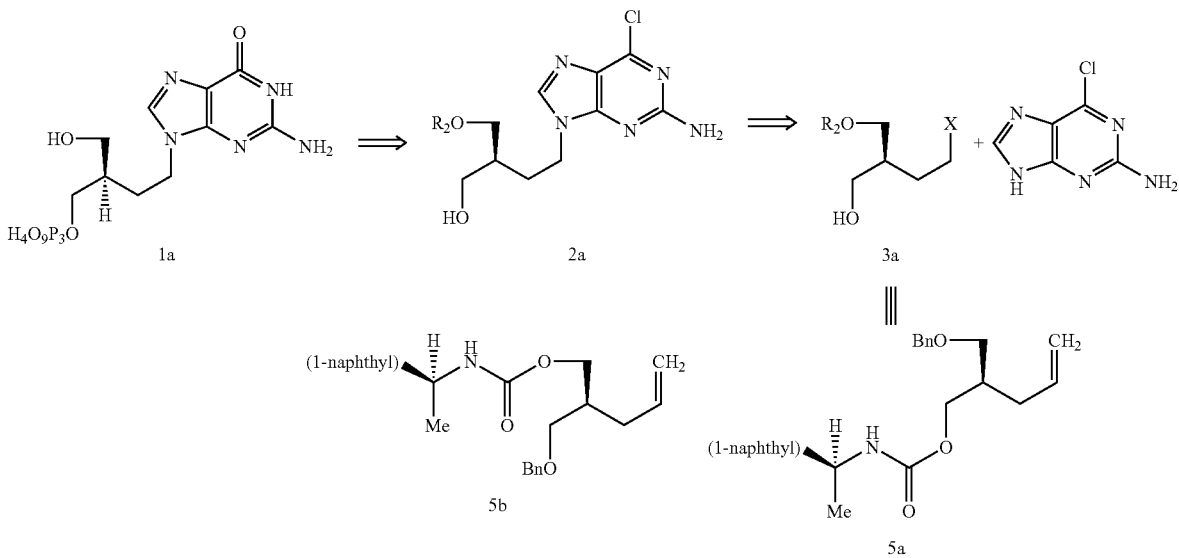

Where: $R_1$ and $R_2$ are orthogonal protecting groups and X = good leaving group The diastereomeric urethanes 5a and 5b were separated by medium pressure column chromatography and were shown by analytical normal phase chromatography to be 86% d.e. in both cases. Reduction of the urethanes 5a and 5b with LAH gave the mono-benzyl ethers 6a and 6b[2]. The optical rotation of the levorotary mono-benzyl ether 6a ($\alpha_D^{22}$ −12.4° (c=1.00, chloroform)); lit.[2] $\alpha_D^{22}$ −12.1° (c=0.68, chloroform)) had previously been established as possesing the S configuration. The mono-benzyl ethers 6a and 6b were silylated with the sterically bulky t-butyldiphenylsilyl group to give 7a and 7b in order to avoid possible silyl migration in later steps. The olefins 7a and 7b were firstly ozonised in good yield to the aldehydes 8a (78%) and 8b (91%) and then reduced to the alcohols 9a and 9b with Dibal-H.

For the synthesis of (R)-penciclovir triphosphate 1a the alcohol 9a was converted to the bromide 10a ($Br_2$, $PPh_3$, DMF, 47%) in moderate yield. Alkylation of 2-amino-6-chloropurine 4 with the bromide 10a, under literature conditions[4], for the preparation of nucleoside H-phosphonates as synthons in oligonucleotide synthesis[6]. Phosphitylation of the nucleoside 14a (90% e.e.) was carried out using the van Boom reagent following conditions similar to that in the literature[8] for the synthesis of nucleoside triphosphates[7]. The phosphitylated intermediate was then reacted with tri-n-butylammonium pyrophosphate followed by oxidation with iodine to give the crude benzyl protected nucleotide triphosphate 15a. Eventually, conditions that allowed the removal of the benzyl protecting group from 15a and which avoided complete hydrolysis of the triphosphate group were found by using a transfer hydrogenation procedure. Fortuitously, the hydrogenolysis of the benzyl group from 15a could be monitored by analytical anion exchange HPLC which yielded not only (R)-penciclovir triphosphate 1a, but also the(R)-diphosphate 16a and the (R)-monophosphate 17a. The latter two penciclovir nucleotides being formed as a result of hydrolysis of the triphosphate group under the transfer hydrogenation reaction conditions.

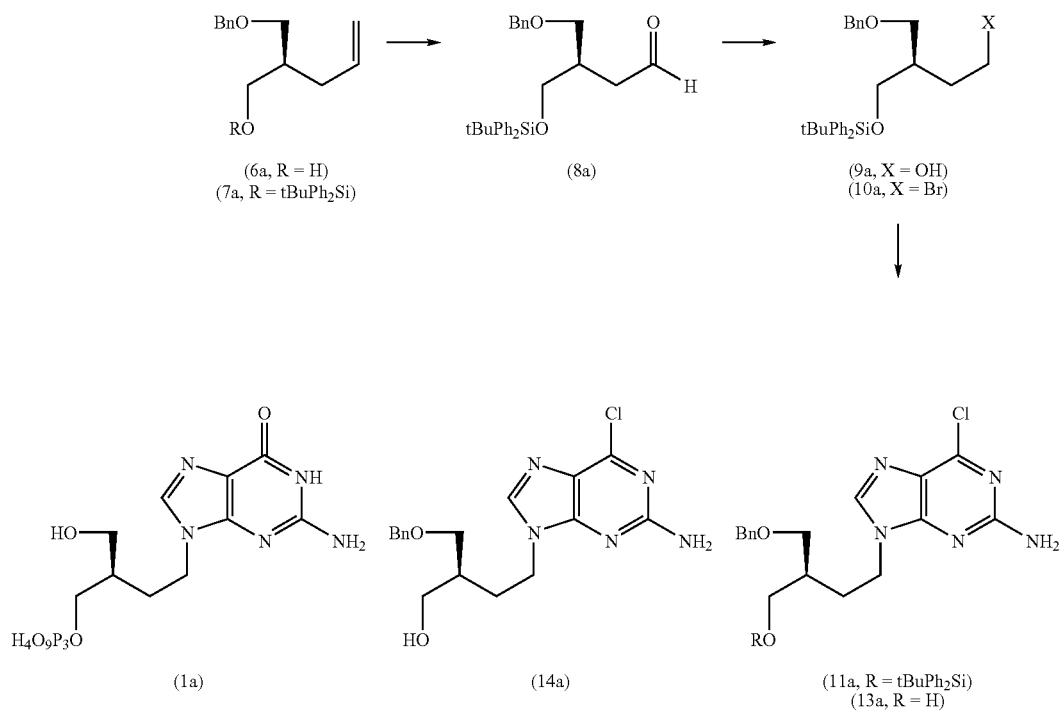

gave as the major product the N-9 alkylated nucleoside 11a (75%) which was separated from the unwanted N-7 isomer 12a (14%) by column chromatography. The regiochemistry of addition was simply confirmed from the undecoupled $^{13}C$ NMR spectrum of (12a)[5]. The optical purity of Ha was not amenable to analysis by chiral HPLC. However, removal of the silyl protecting group of 11a by acidic hydrolysis gave not only the chloropurine 13a (42%, 93% e.e.) but also some of the desired guanosine nucleoside 14a (23%,H94/0223% e.e.) both of which were amenable to chiral HPLC analysis. Prolonged acidic hydrolysis smoothly converted the chloropurine 13a to the guanosine nucleoside 14a (75%). The phosphitylating agent 2-chloro-4H-1,3,2-benzodioxaphosphorin-4-one (van Boom reagent) had previously been used

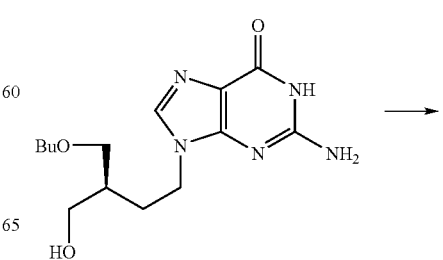

-continued

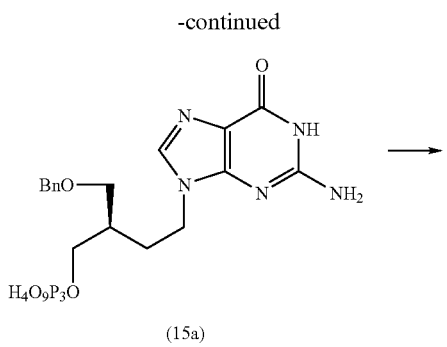

(15a)

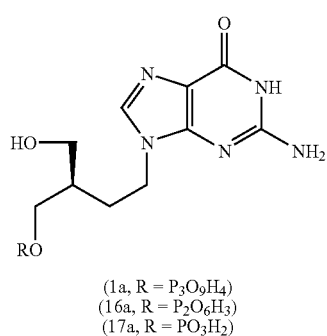

(1a, R = P₃O₉H₄)
(16a, R = P₂O₆H₃)
(17a, R = PO₃H₂)

The synthesis of the (S)-triphosphate 1b was carried out under essentially identical conditions to those described for the synthesis of the (R)-triphosphate 1a, except that the alcohol 9b was converted firstly to the mesylate 9c and then to the iodide 10b. Alkylation of 2-amino-6-chloropurine 4 with 10b again yielded the N-9 adduct 10b as the major product along with a small amount of the unwanted N-7 adduct adduct 12b. Acidic hydrolysis of 10b yielded a small amount of the 6-chloropurine 13b (6%) but mainly the desired guanosine nucleoside 14b (85%).

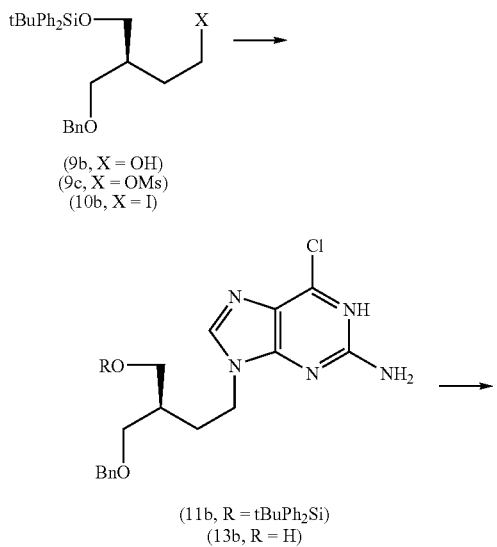

(9b, X = OH)
(9c, X = OMs)
(10b, X = I)

(11b, R = tBuPh₂Si)
(13b, R = H)

-continued

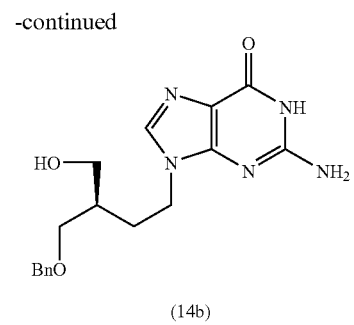

(14b)

Phosphitylation of 14b (90% e.e.) with the van Boom reagent, followed by reaction with tri-n-butylammonium pyrophosphate and then iodine gave the crude triphosphate 15b. Again transfer hydrogenation of 15b was monitored by analytical anion exchange HPLC to yield not only the desired (S)-penciclovir triphosphate 1b but also the (S)-diphosphate 16b and the (S)-monophosphate 17b. The optical rotation results of all the (R)- and (S)-penciclovir phosphates are shown in Table 1. For each enantiomeric pair the magnitude and sign of the optical rotations are essentially equal and opposite. This suggests that there has been little or no loss of chiral integrity from the precursors 14a and 14b, 90% e.e. in both cases, during the transfer hydrogenation conditions and therefore the optical purity of 1a, 1b, 16a, 16b, 17a and 17b to be approximately 90% e.e. in each case.

Method A:

Spherisorb silica (250×5.0 mm). Buffer A, Hexane; buffer B, hexane:methylene chloride (1:1); buffer C, hexane:ethanol (80:20). Eluant isocratic 40% A: 59%: 1% C, 1.00 ml/min. U.V. detection 220 n.m.

Retention time 5a (major 9.48 mins, minor 8.98 mins), 5b (major 9.23 mins, minor 9.69 mins)

Method B:

Merck RP select B (125×4 mm) uM. Buffer A, TFA (0.1%) in water, buffer B TFA (0.1%) in acetonitrile. Eluant, gradient running from 5% to 80% B over 40 minutes, then 10 minutes at 80% B. Flow 2.00 ml/min. U.V. detection at 215 n.m.

Method C:

Chiralpak AD (250×4.6 mm). Eluant isocratic hexane:ethanol (7:3), 1.00 ml/min. u.v. detection at 220 n.m.

Method D:

Chiralpak AD (250×4.6 mm). Eluant isocratic hexane:ethanol (1:1) containing 0.1% DEA, 1.0 ml/min. U.V. detection at 240 n.m.

Method E:

Chiracel OB (250×4.6 mm). Eluant isocratic hexane:ethanol (98:2), 1.00 ml/min. U.V. detection 220 n.m.

Method F:

Chiracel OC (250×4.6 mm) isocratic hexane:ethanol (95:5) containing 0.1% DEA, 1.00 ml/min.U.V. detection at 220 n.m.

Method G:

Rainin Hydropore SAX (100×4.6 mm plus precolumn) 12 μm. Buffer A, ammonium phosphate: methanol (9:1, 10 mM, pH 5.7), buffer B, ammonium phosphate: methanol (9:1, 125 mM, pH 5.7). Eluant gradient 0% to 100% B over 25 minutes, 1.00 ml/min. U.V. detection 254n.m.

2-Benzyloxymethyl-4-penten-1-ol (6)

To a stirred solution of sodium hydride (4.765 g, 119.1 mmol) in dimethylformamide (50 ml) under argon with ice bath cooling was added a solution of 2-hydroxymethyl-4-penten-1-ol[8] (11.07 g, 95.3 mmol) in dimethylformamide (75 ml) dropwise over 20 minutes. The cooling bath was removed and stirred for 1H before recooling the solution in an ice bath. A solution of benzylbromide (11.34 ml, 95.3 mmol) in dimethylformamide (75 ml) was added over 5 minutes, and after stirring for 18 hours at room temperature the reaction mixture was poured into brine (1.5 L) and extracted with diethylether (4×300 ml). The organic fraction was washed with water (2×1.0 L), dried over sodium sulphate, filtered and concentrated in vacuo to yield a light brown oil (17.40 g). Silica gel crude oil (500 g) was purified by column chromatography using an increasing gradient from 10% diethylether: hexane 100% diethylether to yield ( ) (11.30 g, 57.5%) as an oil; $^1$H NMR (270 MHz, CDCl$_3$) δ 7.53 to 7.37 (5H, m) aromatic, 5.90 (1H, ddt), 5.15 (2H, m), 4.67 (1H, d), 4.62 (1H, d), 3.89 to 3.69 (3H, m), 3.62 (1H, dd), 2.38 (1H, bs), 2.23 (2H, ddd), 2.09 (1H, m);$^{13}$ (δ(67.8 MHz, CDCl$_3$) 138.00, 136.26, 128.48, 127.76, 127.63, 116.56,73.47, 73.34, 65.73, 40.37, 32.79; m/z (CI) 207 (MH$^+$); C$_{13}$H$_{18}$O$_2$ requires C 75.69, H 8.80 found$^c$ 75.30, H 8.84.

(R)-(+)and (S)-(−)-2-benzyloxymethyl-4-penten-1-ol

To a stirred solution of (±)-2-benzyloxymethyl-4-penten-1-ol (8,52 g, 41.3 mmol) in triethylamine (40 ml, freshly distilled off P$_2$O$_5$) under nitrogen was added (R)-(−)-1-(1-naphthyl)ethylisocyanate (8.00 g, 40.56 mmol). After 16 hours the mixture was filtered and the solid washed with hexane. The filtrate was concentrated in vacuo to yield as a pale yellow 15.46 g. Exhaustive column chromatography on silica gel eluting with methylene chloride: hexane: diethyl ether (10:10:1) gave the faster running diastereomer (5a) (5.15 g, 30.9%) which was shown by analytical normal phase HPLC (Method A) to be 86% d.e. The slower running diastereomer (5b) (5.49 g, 32.9%) was also shown to be 86% d.e. by HPLC (Method A). To a solution of the faster running diastereomer (5a) (5.15 g, 12.76 mmol) in diethyl ether (250 ml) was added solid lithium aluminium hydride (484 mg, 12.76 mmol) and the mixture refluxed for 24H. The mixture was cooled in a water bath and water (0.43 ml) added, then a solution of sodium hydroxide (2.5M, 0.85 ml) and finally more water (1.06 ml). After stirring at room temperature for 20 minutes the mixture was filtered through celite and the filtrate concentrated in vacuo to yield a clear oil (4.89 g). Purification by column chromatography on silica gel eluting with a gradient from methylene chloride: hexane, diethyl ether (5:5:1) to (5:5:2) to yield (S)-(−)-215 benzyloxymethyl-4-penten-1-ol (6a) (1.97 g, 75%). In a similar way the slower diastereomer (5b) (5.49 g, 13.6 mmol) was reduced with lithium aluminium hydride to yield R-(+)-2-benzyloxymethyl-4-penten-1-ol (6b)(2.535 g, 90.3%). (S)-(−)-2-Benzyloxymethyl-4-penten-1-ol (6a)

Produced from lithium aluminium hydride reduction of (5a) faster running diasterethan on TLC in diethyl ether. $[δ^{22}{}_D$–12.44° (chloroform, c=1.00)], [lit α$^{22}{}_D$ 12.1°(c=0.68, chloroform)]. Optical purity by chiral HPLC (Method E), retention time.

(R)-(+)-2-Benzoxymethyl-4-penten-1-ol (6b)

Produced from lithium aluminium hydride reduction of (5b) slower running diastereothan TLC in diethyl ether. Optical purity by chiral HPLC (Method E) % retention time. See comments above.

(S)-2-benzyloxymethyl-1-O-(1-butyldiphenysilyl)-4-pentene (7b)

To a stirred solution of the (R)-(+)-alcohol (6b) (1.67 g, % e.e, 8.1 mmol), under argon, in dimethylformamide (25 ml) was added imidazole (1.213 g, 17.8 mmol) and then t-butyldiphenylchlorosilane (2.448 g, 8.9 mmol). The mixture was stirred at RT for 16H and then poured into dilute brine and extracted with methylene chloride. The organic fraction was dried over sodium sulphate, filtered and concentrated in vacuo to yield a colourless oil (4.18 g). Column chromatography on silica gel eluting with 1% diethylether in hexane yielded (7b) (3.43 g, 95%) as a clear oil.

(R)-2-Benzyloxymethyl-1-O-(t-butyldiphenylsilyl)-4-pentene (7a)

In a similar procedure to that described above the (S)-(−)-alcohol (6a) (1.71 g, 8.90 mmol) was silylated which after column chromatography on silica gel yielded (7a) (2.07 g, 83%) as a clear oil. $^1$H NMR (200 MHz, CDCl$_3$) δ see above

(R)-2-Benzyloxymethyl-1-O-(t-butyldiphenylsilyl) butan-4-al (8a)

To a solution of the silyl protected olefin (1.32 g, 2.99 mmol) (7a) in methylene chloride (60 ml) at −70° C. was bubled ozone gas. After 10 minutes TLC indicated all starting material had been consumed and argon was bubbled through the solution until the exhaust gas was free of ozone. Then add a solution triphenylphosphine (0.94 g, 3.59 mmol) in DCM (10 ml) was added and allowed to slowly warm to RT. After 16H the mixture was concentrated in vacuo to yield a pale yellow oil (3.606 g). Chromatography on silica gel eluting with a gradient of 2% diethylether in hexane to 10% diethyl ether in hexane yielded the title compound (8a) (1.03 g, 78%) as an oil. $^1$H NMR (200 MHz, CDCl$_3$) δ9.75 (1H, t), 7.61 (4H, bd), 7.42 to 7.22 (11H, m), 4.45 (2H, s), 3.67 (2H, m), 3.55 (1H, dd), 3.45 (1H, dd), 2.52 (3H, bs), 1.03 (9H, s).

(S)-2-Benzyloxymethyl-1-O-(t-butylidiphenylsilyl)-butan-4-al (8b)

In a similar method to a solution of the olefin (7b) 3.315 g, 7.46 mmol) in methylene chloride 150 ml under argon, internal temp −68° C. was bubbled ozone gas. After 15 minutes solution went blue. Bubble argon until exhaust gas negative for ozone. After 30 mins add a solution of triphenylphosphine in DCM (30 ml) and allowed to slowly warm to RT and was stirred for 64H. Purified as above to yield (3.03 g, 90%) as a clear oil.

(R)-2-Benzyloxymethyl-1-O-(t-butyldiphenylsilyl)-butan-1-ol (9a)

To a stirred solution of the aldehyde (8a) (2.132 g, 4.80 mmol) in methylene chloride (50 ml) under argon at –70° C. was added a solution of diisobutylaluminium hydride in methylene chloride (1.0M, 5.30 ml) dropwise over 5 minutes. After 1H at –70° C. TLC indicated all starting material consumed. Ethyl aceate (1.77 ml) was then added, followed by water (1.6 ml) and the cooling bath removed and replaced with a water bath. After 20 minutes was added sodium hydrogen carbonate (629 mg, 7.49 mmol) and the mixture stirred for 2.5 h. The solid was removed by filtration and washed with methylene chloride. The filtrate was concentrated in vacuo to yield as a clear oil (9a) (2.2 g, 103%) which was used without further purification. $^1$H NMR (200 MHz, CDCl$_3$) δ 7.64 (4H, bm), 7.44 to 7.25 ($^1$H, m), 4.48 (2H, s), 3.65 (4H, m), 3.60 (1H, dd), 3.45 (1H, dd), 2.73 (1H, bt), 2.02 (1H, m), 1.67 (2H, m), 1.04 (9H, s).

(S)-2-benzyloxymethyl-1-O-(t-butyldiphenylsilyl)-butan-1-ol (9b)

To a solution of the crude aldehyde in DCM (71 ml) at –68° C. under argon was added dibal-H via syringe over 5 minutes. After 4.25 h TLC indicated all starting material had been consumed and was quenched by addition of EtOAc (2.50 ml). The cooline bath was removed and replaced with a water bath and mixture stirred for a further 0.5H. Then solid sodium hydrogen carbonate (0.893 g, 10.63 mmol) was added and stirred for a further 1H. The solid was removed by filtration and washed with methylene chloride to yield (9b) as a crude oil (2.89 g, 95%) which was used without further purification.

(R)-2-Benzyloxymethyl-1-O-(t-butyldiphenylsilyl)-4-bromobutane (10a)

To a stirred solution of the alcohol (2.142 g, 4.80 mmol) and triphenylphosphine (1.386, 5.29 mmol) in dimethylformamide was added bromine (0.272 ml, 5.29 mmol) dropwise. After stirring for 16H at RT the mixture was poured into water, the solid was filtered and washed with hexane. The aqueous fraction was washed with hexane and the combined organic fractions were dried over sodium sulphate and concentrated in vacuo to give a pale yellow oil (2.98 g). Column chromatography on silica gel eluting with a gradient from 5% to 25% methylene chloride in hexane to yield the title compound (9a, 1.14 g, 46.7%) as an oil. $^1$H NMR (250 MHzCDCl$_3$) δ 7.65 (4H, m), 7.47 to 7.24 (11H, m), 4.48 (2H, s), 3.69 (2H, m), 3.53 (2H, m), 3.42 (2H, t), 2.12 to 1.92 (3H, m), 1.04 (9H, s).

(R)-2-benzyloxymethyl-1-O(t-butyldiphenylsilyl)-butan-4-O-methane sulphonate (9c)

To a stirred solution of the crude alcohol ( ) (2.894 g, 6.45 mmol) in methylene chloride and triethylamine (1.35 ml, 9.68 mmol) under argon at –5° C. was added methane sulphonyl chloride (0.6° ml, 7.74 mmol) dropwise over 7 minutes. The mixture was warmed to 5° C., stirred for a further 1.5 h, cooled to 0° C. and dilute hydrochloric acid (1.25M) added. The organic phase was separated and the aqueous phase extracted with methylene chloride. The total organic fraction was washed with dilute sodium hydrogen carbonate solution, dried over sodium sulphate, filtered and evaporated in vacuo to yield a pale yellow oil (3.40 g) which was used without further purification. $^1$H NMR (200 MHz) δ 7.63 (4H, m), 7.45 to 7.23 (11H, m), 4.47 (2H, s), 4.26 (2H, dt), 3.68 (2H, m), 3.52 (2H, m), 2.88 (3H, s), 2.01 (1H, m), 1.88 (2H, m), 1.04 (9H, s).

(R)-2-benzyloxymethyl-1-O-(t-butyldiphenylsilyl)-4-iodo-butane (10b)

To a stirred solution of the mesylate (9c) (3.40 g) (6.45 mmol) in acetone (60 ml), under nitrogen, was added sodium iodide (1.934 g, 12.9 mmol). The mixture was then heated under reflux for 3.5 h, cooled to RT and concentrated in vacuo. Methylene chloride and water were added, separated and the aqueous phase back extracted with methylene chloride. The organic phase was separated and the aqueous phase was washed first with sodium metabisulphite and then brine and dried over sodium sulphate. The solvent was removed in vacuo to yield a pale yellow oil (3.391 g). Column chromatography on silica gel eluting with a gradient of 2% diethyl ether in hexane to 5% diethyl ether in hexane yielded the title compound (10b) (2.740 g, 76%) as a clear oil. $^1$H NMR (200 MHz, CDCl$_3$) δ 7.63 (4H, m), 7.45 to 7.22 (11H, m), 4.47 (2H, s), 3.69 (2H, m), 3.54 (2H, m), 3.18 (2H, br), 1.97 (3H, m), 1.04 (9H, s).

(R)-2-benzyloxymethyl-1-O-(t-butyldiphenylsilyl)-4-(2-amino-6-chloropurin-9-yl)-butane(11a)

To a stirred solution of the bromide (10a) (1.017 g, 2.00 mmol) in dimethylformamide (9.20 ml) and 2-amino-6-chloropurine (0.340 g, 2.00 mmol) at RT under argon was added potassium carbonate (0.415 g, 3.00 mmol). After 22H the reaction mixture was poured into water and extracted with methylene chloride:methanol (99:1). The combined organic extracts were washed with brine, dried over sodium sulphate, filtered and concentrated in vacuo to give a yellow oil (1.287 g). Column chromatography on silica gel eluting with a gradient from 1% to 3% methanol in methylene chloride to yield (11a)as an oil (0.90 g, 75.1%). $^1$H NMR (200 MHz, CDCl$_3$) δ 7.62 (5H, m), 7.48 to 7.22 (11H, m), 5.04 (2H, bs), 4.47 (2H, s), 4.10 (2H, t), 3.69 (2H, d), 3.48 (1H, dd), 3.37 (1H, dd), 2.09 to 1.78 (3H, m), 1.04 (9H, s).

(S)-2-benzyloxymethyl-1-O-(t-butyldiphenylsilyl)-4-(2-amino-6-chloropurin-9-yl)-butane (11b)

To a stirred solution of the iodide (10b) (2.40 g, 4.90 mmol) in dimethylformamide (22.5 ml) was added 2-amino-6-chloropurine (834 mg, 4.91 mmol) and potassium carbonate (1.01 g, 7.38 mmol) under argon at RT. After 30H was added methanol:methylene chloride (1:99, 250 ml) and the mixture poured into water (1 L). The aqueous fraction was back extracted with methanol:methylene chloride (1:99, 3×250 ml). The total organic fraction was dried over sodium sulphate, filtered and concentrated in vacuo to give an oil (11.0 g, containing residual dimethylformamide). The oil was taken up in methylene chloride (200 ml) and washed with water (1 L). The aqueous phase was back extracted with methylene chloride (3×200 ml). The combined organic phase was again washed with water (1 L), dried over sodium sulphate, filtered and concentrated in vacuo to give a yellow oil (3.162 g). Column chromatography on silica gel eluting with DCM, methanol:methylene chloride (1:99) and finally methanol:methylene chloride (1.5:98.5) gave (11b) (2502 g, 85%) as an oil containing ~5% DMF by $^1$H NMR)

(R)-2-benzyloxymethyl-1-O-(t-butyldiphenylsilyl)-4-(2-amino-6-amino-7-yl)butane (12b)

The title compound was obtained as a later eluting fraction from the silica gel column purification of (11b). The resulting oil was recrystallised from ethyl acetate:hexane to give a white solid (457 mg, 15.6%) m.pt. 109–110C, HPLC purity (Method) 98.0%. m/z 603 (M+H). $^1$H NMR (400 MHz, DMSO-$d_6$) 8.33 (1H, s), 7.54 (4H, m), 7.48 to 7.23 (11H, m), 6.61 (2H, bs), 4.42 (2H, t), 4.37 to 4.27 (2H, m), 3.64 (2H, m), 3.50 (2H, m), 1.95 (1H, m), 1.83 (2H, m), 0.93 (9H, s), $^3$C (100.6 MHz, DMSO-$d_6$) 164.25, 159.84, 149.18, 1.42.03, 138.28, 134.91, 132.86, 132.82, 129.71, 128.10, 127.73, 127.25, 127.22, 114.61, 72.06, 69.42, 63.64, 44.51, 38.83, 29.92, 26.49, 18.65.

(S)-2-benzyloxymethyl-4-(2-amino-6-chloropurin-9-yl)-butan-1-ol (13a)

To a stirred solution of (11a) (158 mg, 0.27 mmol) in tetrahydrofuran (4.0 ml) was added hydrochloric acid (2M, 4.0 ml) under argon at RT. After 24H excess saturated sodium carbonate was added. The aqueous phase was extracted with ethyl acetate and then chloroform. The total organic fraction was dried over sodium sulphate, filtered and evaporated to give a clear oil (135 mg). Column chromatography on silica gel eluting with an increasing gradient of methanol 2% to 4% methanol in methylene chloride to yield (13a) (60 mg, 66%) as an oil. A sample was recrystallised from ethyl acetate:hexane to yield a white solid. $^1$H NMR (400 MHz, CDCl$_3$) δ 7.74 (1H, s), 7.42 to 7.28 (5H, m), 5.11 (2H, bs), 4.50 (2H, dd), 4.17 (2H, m), 3.75 (2H, d), 3.56 (2H, m), 2.45 (1H, bs), 2.08 to 1.90 (2H, m), 1.83 (1H, m), m/z (FAB) 362 (M+H). Chiral HPLC (Method C) 93.6% e.e.

(S)-2-benzyloxymethyl-4-(9-guaninyl)-butan-1-ol (14a)

To a stirred solution of the chloropurine (13a) (325 mg, 0.9 mmol) in tetrahydrofuran (15 ml) was added hydrochloric acid (2M, 15 ml) and stirred at 60° C. under argon, for 26H. The reaction mixture was cooled in a water bath and sodium hydroxide solution (10M) added until pH9. The aqueous phase was extracted with methanol:ethyl acetate. (7:93, 4×35 ml). The organic phase was dried over sodium sulphate, filtered and evaporated in vacuo to give an oil (150 mg). On standing a white solid crystallised from the aqueous phase which was filtered off, washed with water (5 ml) and diethylether and dried in vacuo to give the title compound (14a) (175 mg, 56.8%). $^1$H NMR (400 MHz, DMSO-$d_6$) 10.55 (1H, s), 7.66 (1H, s), 7.40 to 7.22 (5H, m), 6.44 (2H, bs), 4.51 (1H, t), 4.42 (2H, t), 4.00 (2H, t), 3.49 to 3.30 (4H, m), 1.76 (2H, q), 1.64 (1H, m). HPLC purity (Method) 98.3%, chiral HPLC (Method D) 89.6% e.e., retention time major peak 10.3 mins, minor peak 6.9 minutes. ($C_{17}H_{11}N_5O_3$,−7.7 ppm, $NH_3Cl$) m/z 343.1617. The oil was purified by column chromatography on silica gel eluting with an increasing gradient of methanol (8–22%) in methylene chloride to yield (14a) (87 mg, 28.2%) as an oil.

(R)-2-benzyloxymethyl-4-(2-amino-6-chloropurin-9-yl)-butan-1-ol (13b)

To a stirred solution of (11b) (248 mg, 0.42 mmol) in THF (6.22 ml), at RT under argon, was added hydrochloric acid (2.0M, 6.2 ml). After 26H the tetrahydrofuran was removed in vacuo. The aqueous phase was extracted with ethyl acetate (3×30 ml), and the total organic fraction dried over sodium sulphate, filtered and evaporated in vacuo to give an oil. Column chromatography on silica gel eluting with chloroform and then an increasing gradient of methanol (1 to 4%) gave (13b) (96 mg, 63.8%). The resulting oil was recrystallised from ethyl acetate:hexane to give a white solid (86 mg, 57.2%). Chiral HPLC (Method C) 86.2% e.e.

(R)-2-benzyloxymethyl-4-(9-guaninyl)-butan-1-ol (14b)

To a stirred solution of the chloropurine (11b) (2.235 g, 3.71 mmol) in tetrahydrofuran (56 ml), under argon at RT, was added hydrochloric acid (2.0M, 56 ml). The mixture was heated in the region 65–70° C. for 20 hours, cooled to RT and neutralised with sodium hydroxide (12.5M, ca 9 ml) until pH7. The tetrahydrofuran was removed by evaporation in vacuo. The aqueous phase was extracted with methylene chloride (100 ml) producing an emulsion and solid was removed by filtration. The solid was washed with methylene chloride (100 ml) and diethyl ether (50 ml). The aqueous phase was back extracted with methylene chloride (100 ml, from solid wash). The combined organic extracts were dried over sodium sulphate, filtered, and concentrated in vacuo to give an oil (1.616 g). The aqueous phase was readjusted to pH 7 and cooled in an ice bath for 2H. The resulting solid was washed with water and diethyl ether and combined with the first crop. The combined solid were taken up in methanol, filtered and concentrated in vacuo to give (14b) (944 mg, 74.5%). HPLC purity 98.2%, chiral HPLC (Method D), 81.4% e.e. A sample (755 mg) was recrystallised from water (ca 90 ml) and allowed to slowly cool to RT. The resulting solid was filtered, washed with water and dried in vacuo to give (14b) (609 mg, 80.7% recovery). Chiral HPLC (Method D) 89.9% e.e. retention time major peak 6.7 mins, minor peak 10.4 mins. HPLC purity (Method B) 98.9%. $C_{17}H_{21}N_5O_3(H_2O)_{0.6}$, requires C=57.43; H=6.29 and N=19.70 found C=57.49, H=6.07 and N=19.72.

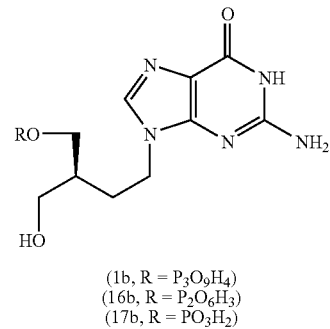

(1b, R = $P_3O_9H_4$)
(16b, R = $P_2O_6H_3$)
(17b, R = $PO_3H_2$)

(S)-Penciclovir triphosphate (1b), diphosphate (16b) and monophosphate (17b)

A suspension of the (R)-nucleoside (14b) (174 mg, 0.51 mmol) was azeotroped with pyridine (2×10 ml). To a stirred suspension of ( ) in pyridine (1.22 ml) and dimethylformamide (4.62 ml) was added a solution of 2-chloro-4H-1,3,2-benzodioxaphosphorin-4-one (113 mg, 0.57 mmol) in dioxane (1.13 ml, plus 0.5 ml wash). The nucleoside immediately started to dissolve and a slight yellow colour was observed. After 10 minutes a solution of tri-n-butylamine pyrophosphate (336 mg) in tri-n-butylamine (0.58 ml) and dimethylformamide (2.9 ml) was added. After a further 10 minutes a solution of iodine (1% w:v) in pyridine:water (98:2;v:v; 10.2 ml) was added. Fifteen minutes after the addition of the iodine the reaction was poured into water (80 ml) and extracted with chloroform (4×80 ml). The aqueous phase was concentrated in vacuo to give the crude benzyl protected triphosphate (11b) (460 mg). To a soution of the crude triphosphate ( ) (460 mg) in water:methanol (1:1, 80 ml) was added palladium on carbon catalyst (Johnson-Matthey, Type 487L, 174 mg) with stirring under argon. After 15 minutes the ctalyst was removed by filtration on celite and washed with not methanol:water (1:1, 90 ml). To the filtrate was added ammonium formate (1.0 g) and palladium catalyst (203 mg), with stirring under argon. The mixture was heated at reflux, both temperature 93–103° C., for 6H. At which time the reaction had only proceeded ~50% to completion as judged by anion exchange HPLC (method). The hot reaction mixture was filtered through celite and the catalyst washed with hot water:methanol (1:1, 200 ml). The filtrate was concentrated in vacuo and lyopholysed from water (700 ml) to give a white solid (620 mg). This solid was re-submitted to the transfer hydrogenation conditions. To a solution of the crude partially deprotected triphosphate (620 mg). This solid was re-submitted to the transfer hydrogenation conditions. To a solution of the crude partially deprotected triphosphate (620 mg) in water:methanol (1:1, 160 ml) was added ammonium formate (480 mg) and palladium catalyst (50 mg), with stirring under argon. The mixture was heated, oil bath temperature 80° C., for 1.5H after which time the deprotection had deemed to have gone to completion, ≦1% ( ) remaining, as judged by anion exchange HPLC. The hot reaction mixture was filtered through celite and the catalyst washed with hot water:methanol (1:1, 200 ml). The filtrate was concentrated in vacuo to give a white solid (900 mg) which was lyopholysed from water (1×500 ml and 1×150 ml) to give crude (1b), (16b) and (17b) (367 mg).

Half of this was purified to give:
50 mg PCV.TP
40 mg PCB.DP
10 mg PCV.MP

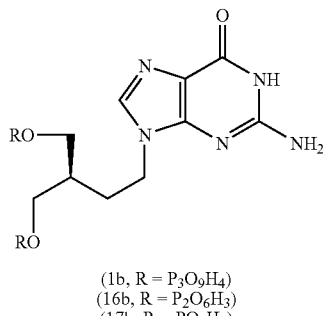

(1b, R = $P_3O_9H_4$)
(16b, R = $P_2O_6H_3$)
(17b, R = $PO_3H_2$)

(R)-Penciclovir triphosphate (1a), diphosphate (16a) and monophosphate (17a)

The (S)-nucleoside (14a) (174 mg, 0.51 mmol) was phosphenylated and converted to the crude benzyl protected (15a) under identical conditions to those described for the synthesis of its enantiomer (15b) above. The crude benzylated triphosphate (15a) was taken up in water:methanol (1:1, 80 ml) and stirred with palladium on carbon catalyst (Type 487L, 175 mg). After 20 minutes the mixture was filtered through celite and the catalyst washed with water: methanol (1:1, 80 ml). The filtrate was used for the transfer hydrogenation debenzylation reaction. To the filtrate (160 ml) was added ammonium formate (530 mg) and palladium on carbon catalyst (153 mg) and stirred under argon. The mixture was heated, oil bath temperature 76–88° C., and monitored by anion exchange HPLC (Method). After 3.5H palladium catalyst (305 mg) was added and after 5.5H extra palladium catalyst (142 mg) was added. After 6.5H the reaction was filtered through celite and the catalyst washed with hot water:methanol (1:1, 200 ml) and the filtrate concentrated in vacuo. The filtrate was dissolved in water: methanol (1:1, 160 ml), ammonium formate (265 mg) and palladium catalyst (150 mg). The mixture was stirred under argon and heated in an oil bath in the region 76–80° C. After 5.5H the deprotection had deemed to have gone to completion by anion exchange HPLC, ≦1% ( ) remaining. The hot reaction mixture was filtered through celite and the catalyst washed with hot methanol:water (1:1, 100 ml). The filtrate was concentrated in vacuo, azeotroped with water (25 ml) to give an oil (830 mg). Then lyopholysed from water (1×300 ml and 1×125 ml) to give a white solid (376 mg).

REFERENCES

1. Sime, J. T., Barnes, R. D., Elson, S. W., Jarvest, R. L. and O'Toole, K. J., *J. Chem. Soc. Perkin Trans.* 1, 1992, 1653–1658; Hannah, J., Tolman, R. L., Karkas, J. D. Liou, R., Perry, H. C. and Field, A. K., *J. Heterocyclic Chem.*, 1989, 26, 1261–1276.
2. Furuyama, T., Wang, C.-L. J. and Kishi, *J. Am. Chem. Soc.*, 1979, 101, 260–262.
3. Harnden, M. R. and Jarvest, R. L., *J. Chem. Soc. Perkin Trans* 1, 1991, 2071–2079.
4. Harnden, M. R., Jarvest, R. L., Bacon, T. H. and Boyd, M. R., *J. Med. Chem.*, 1987, 30, 1636–1642; Geen, G. R., Grinter, T. J., Kincey, P. M. and Jarvest, R. L., *Tetrahedron*, 1990, 46, 6903–6914.
5. In the undercoupled $^{13}C$ NMR of ( ) the purine C-5 (114.53 ppm) is coupled to purine H-8 and to the methylene group (C-4) of the butylside change and appears as a quartet. Where as the purine C-4 (164.12 ppm) appears as a doublet as it is only coupled to the proton on C-8 of the purine.
6. Marugg, J. E., Tromp, M., Kuyl-Yeheskiel, E., van der Marel, G. A. and Van Boom, J. H., *Tetrahedron Lett.*, 1986, 27, 2661–2664.
7. Ludwig, J. and Eckstein, F., *J. Org. Chem.*, 1989, 54, 631–635.
8. Wasson, B. K., Gleason, C. H., Levi, I, Parker, J. M., Thompson, L. M. and Yates, C. H., *Can. J. Chem.* 1961, 39, 923–932.

Description 2-preparation of (R)-PCV phosphate-alternative method 9-(4-Hydroxy-3-O-monomethoxytritylmethylbut-1-yl)guanine. (9-S and 9-R)

9-(4-O-Isobutyryl-3-hydroxymethylbut-1-yl)guanine (4-R, peak 1 or 4-S, peak 2, respectively) (0.3 g, 0.9 mmol) was dried under high vacuum for 2 h then was dissolved in DMF (3 mL). To the resultant solution NN-dimethylformamide dimethyl acetal (0.75 mL, 5.5 mmol) was added. The reaction mixture was left overnight at room temperature. The reaction progress was followed by UV (disappearance of the maximum at λ254 nm, and appearance of a new maximum at =301 nm, corresponding to exoamino protected 4-R or 4-S). After reaction completion DMF was evaporated under reduced pressure then residue dissolved in anhydrous pyridine (5 mL). To the resultant solution monomethoxytritylchloride (0.3 g, 0.95 mmol) was added. The reaction mixture was maintained at room temperature overnight then concentrated solution of $NH_4OH$ (5 mL) was added. The whole was left overnight (the maximum at $\lambda=301$ disappeared) then solvents were evaporated under reduced pressure. The oily reisidue was dissolved in $CH_2Cl_2$ (10 mL), and the solution was extracted with $H_2O$ (3×5 mL). The organic fraction was dried over $MgSO_4$ then $CH_2Cl_2$ evaporated. Crude 9-(4-O-isobutyryl-3-O-monomethoxytritylmethyl-but-1-yl)guanine (7) was redissolved in $CH_2Cl_2$ then added dropwise to hexane. The precipitate was filtered, dried under reduced pressure. The yield was 0.3 g of each isomer of 7. Compound 7 (0.3 g) was dissolved in DMF (7.5 mL) and $CH_3OH$ (7.5 mL) then to the resultant solution 1 M NaOH (3 mL) was added to remove the isobutyryl-protection. After 3 h at room temperature the reaction mixture was neutralized with Dowex 50W×8 (pyridinium form). The resin was filtered then washed with $CH_3OH$. The filtrate and washings were combined and solvents evaporated under reduced pressure. Crude 9 was purified by silica gel column chromatography using stepwise gradient of $CH_3OH$ in $CH_2Cl_2$ from 0 to 8% as eluting solvent system. Yield of 9-R was 0.11 g (25%) and 9-S 0.26 g (55%). 9-R: TLC ($CH_2Cl_2$/$CH_3OH$, 9:1) $R_f$ 0.12; UV (95% $C_2H_5OH$), 4235, $\lambda_{min}$ 224, $\lambda_{sh}$ 246, 263; 9-S: TLC ($CH_2Cl_2$/$CH_3OH$, 9:1) $R_f$ 0.12; UV (95% $C_2H_5OH$), $\lambda_{max}$ 235, $\lambda_{min}$ 223, $\lambda_{sh}$ 243, 263.

Note: MMTrPCV (9) was synthesised both, with and without guanine exoamino-group protection. The yields are comparable.

9-(4-Hydroxy-3-hydroxymethyl-but-1-yl)guanine triphosphate (10-R and 10-S)

9-(4-Hydroxy-3-O-monomethoxytritylmethyl-but-1-yl)guanine (9-S or 9-R) (60 mg, 0.11 mmol) was dried under vacuum overnight at room temperature then DMF (3.6 mL) and anhydrous pyridine (1.2 mL) was injected through the septum into the reaction flask equipped with stirring bar. During all the manipulations a small positive pressure of nitrogen was maintained in the reaction vessel by connecting it with a nitrogen-filled balloon. Freshly prepared 1 M solution of 215 chloro-4H-1,2,3-dioxaphosphorin-4-one (5) in anhydrous dioxane (0.55 mL) was injected into well-stirred solution of 9. After 15 min a 0.5 M solution of bis(tri-n-butylammonium)pyrophosphate (6) in anhydrous DMF (1.5 mL), followed by tri-n-butylamine (1 mL) was quickly injected. After 15 min the reaction mixture was divided into two equal parts (3.9 mL each) and to one 25% solution of iodine in pyridine/THF containing water was added till excess of iodine was reached. An excess iodine was destroyed after 15 min by adding a few drops of 5% $NaHSO_3$ aqueous solution, and the reaction mixture was evaporated to dryness. The residue was redissolved in $H_2O$ (5 mL). After standing for 30 min at room temperature the solution was evaporated to dryness then 80% AcOH (25 mL) was added. Reaction mixture was maintained at room temperature for 0.5H then AcOH was coevaporated with n-BuOH to dryness. The residue was treated with $H_2O$ (8 mL) then the resultant suspension was extracted with $CH_2Cl_2$ (3×2 mL). The $H_2O$ fraction containing product was separated and filtered through Acrodisc LC 13 PVDF (0.45 μm, Gelman). The crude PCVTP was purified by FPLC using HiLoad 26/10, Q Sepharose Fast Flow Pharmacia column. The column was eluted with gradient of TEAB buffer (pH 7.0) from 0.05 to 0.7 M, at flow rate 10 mL/min. Fractions containing product were collected and lyophilized. Yield of PCV triphosphate 10-R and 10-S was 90 $A_{260}$ units each (ca. 3.5 mg assuming $\epsilon_{PCVTP}=11.5\times10^3$). 10-R: UV ($H_2O$) $\lambda_{max}$ 253, $\lambda_{sh}$ 262; HPLC (column: 4.6×100 mm, Rainin Hydropore SAX, gradient: from 10% 10 mM $NH_4K_2PO_4$ containing 10% $CH_3OH$ to 125 mM $NH_4K_2PO_4$ containing 10% $CH_3OH$ in 15 min, pH 5.5, flow 1 mL/min, detection: 254 nM) $R_t$ 9.8; MS/ESI 492.0 [M–H]. 10-S: UV ($H_2O$) $\lambda_{max}$ 252, $\lambda_{max}$ 265; HPLC (column: 4.6×100 mm, Rainin Hydropore SAX, gradient: from 10% 10 mM $NH_4K_2PO_4$, 10% $CH_3OH$ to 125 mM $NH_4K_2PO_4$, 10% $CH_3OH$ in 15 min, pH 5.5; flow 1 mL/min, detection: 254 nm) $R_t$ 9.0; MS/ESI 492.0 [M–H].

The invention claimed is:

1. A method of treatment of
   i) HIV-1 infections in mammals, including humans; or
   ii) HBV infections in mammals, including humans;
   which method comprises the administration to the human in need of such treatment, an effective amount of the (R)-enantiomer of the triphosphate of a compound of formula (A):

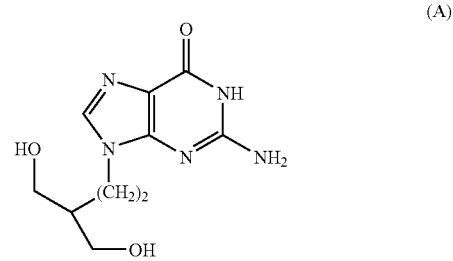

((R)-PCT-TP), or a pharmaceutically acceptable salt thereof:

wherein the (R)-PCV-TP is in the form of a bioprecursor which is a PL-ASOR derivative, phospholipids derivative, (R)-MP Bis(POM) derivative, (R)-MPT diphenyl ester derivative, or dimyristoylglycerol diphosphate derivative of (R)-PCV-MP which liberates intracellularly (R)-PCV-MP which is in turn converted to (R)-PCV-TP.

2. The method according to claim 1 wherein the bioprecursor is a PL-ASOR derivative.

3. The method according to claim 1 wherein the bioprecursor is a phospholipids derivative.

4. The method according to claim 1 wherein the bioprecursor is a (R)-MP Bis(POM) derivative.

5. The method according to claim 1 wherein the bioprecursor is a (R)-MP diphenyl ester derivative.

6. The method according to claim 1 wherein the bioprecursor is a dimyristoylglycerol disphosphate derivative.

* * * * *